United States Patent [19]

Eriksson et al.

[11] 4,215,113

[45] Jul. 29, 1980

[54] METHOD FOR COMBATING VIRUS INFECTIONS

[75] Inventors: Bertil F. H. Eriksson, Södertälje; Åke J. E. Helgstrand, Enhörna; Alfons Misiorny, Bandhagen; Göran B. Stening; Stig-Åke A. Stridh, both of Södertälje, all of Sweden

[73] Assignee: Astra Lakemedel Aktiebolag, Södertälje, Sweden

[21] Appl. No.: 807,783

[22] Filed: Jun. 20, 1977

[30] Foreign Application Priority Data

Jul. 1, 1976 [SE] Sweden .............................. 7607496

[51] Int. Cl.$^2$ .............................................. A61K 31/66
[52] U.S. Cl. ................................................... 424/212
[58] Field of Search .......................................... 424/212

[56] References Cited

U.S. PATENT DOCUMENTS

| 3,767,795 | 10/1973 | Schleicher et al. ................... 424/212 |
| 3,836,650 | 9/1974 | Schleicher et al. ................... 424/212 |

*Primary Examiner*—Jerome D. Goldberg
*Attorney, Agent, or Firm*—Brumbaugh, Graves, Donohue & Raymond

[57] ABSTRACT

A method for the selective treatment of virus infections in animals and man, comprising administering to a host so infected a therapeutically effective amount of phosphonoformic acid or a physiologically acceptable salt thereof.

17 Claims, No Drawings

METHOD FOR COMBATING VIRUS INFECTIONS

FIELD OF THE INVENTION

The present invention relates to novel pharmaceutical compositions and to a novel method for selectively combating virus infections such as influenza virus infections, herpes virus infections, etc. in animals including man.

GENERAL OUTLINE OF THE INVENTION

There are mainly three approaches for the prophylactic and/or therapeutic treatment of virus infections, namely by use of vaccines, by use of chemotherapeutic agents, and by use of interferon. Of these, vaccines and chemotherapeutic agents have gained the largest medicinal use.

However, the existing vaccines, in particular the influenza vaccines, are not deemed to be sufficiently effective. With regard to influenza virus, this is partly because it is difficult to prepare a vaccine in time against a prevailing modified influenza virus. No antiviral chemotherapeutic agent exhibiting good antiviral effect and acceptable side effects has yet been found. One especially undesired effect with available chemotherapeutic antiviral agents is that they may interact not only with the virus but also with components in the host cell.

An effective selective antiviral agent with acceptable side effects should have a selective inhibiting effect on a specific viral function of the virus to be combated. It is, therefore, one object of the present invention to provide a novel method for combating virus infections using an antiviral agent which exerts a selective inhibiting effect on viral functions but which exerts only a negligible inhibiting effect on functions of the host cells.

The invention also relates to novel pharmaceutical compositions containing the antiviral agent.

Although the present invention relates broadly to a novel method for selectively combating virus infections in animals and man, and pharmaceutical preparations to be used at such treatment, it will be particularly useful in the treatment of herpes virus infections and influenza virus infections.

Influenza is one of the most frequent diseases of man, but it is so far very difficult to prevent or treat.

There are two major varieties of influenza, commonly designated influenza A and influenza B. Another variety of influenza, designated influenza C also exists, but is not as frequently occuring as influenza A and B. These types of influenza are caused by virus commonly denoted influenza virus type A, B and C, respectively.

An especially important area of use for the compositions of the present invention is in the treatment of herpes virus infections. Among the herpes viruses may be mentioned Herpes simplex type 1 and 2, varicella (Herpes zoster), virus causing infections mononucleosis (i.e. Epstein-Barr virus) and cytomegalovirus. Other herpes infections to which the present invention is applicable are Herpes dermatitis, Herpes genitalis, Herpes keratitis, and Herpes encephalitis. Other areas of use for the compositions of the present invention are in the treatment of infections caused by viruses such as papaloma virus (i.e. warts), adenoviruses, poxviruses, hepatitis virus A and hepatitis virus B. Other possible areas of use for the compositions of the present invention are in the treatment of infections caused by picornaviruses, arboviruses, leucoviruses, arenaviruses, coronaviruses, rhabdoviruses and paramyxoviruses and for inhibiting the growth of virus transformed cells in animals and man.

DETAILED DESCRIPTION OF THE INVENTION

It has been found according to the present invention that phosphonoformic acid of the structural formula

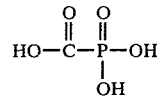

$$\text{HO}-\overset{\overset{\displaystyle O}{\|}}{C}-\overset{\overset{\displaystyle O}{\|}}{\underset{\underset{\displaystyle OH}{|}}{P}}-\text{OH} \qquad \text{I}$$

and physilogically acceptable salts thereof, selectively inhibits certain viral functions which are essential for the replication of the virus.

It has been found that phosphonoformic acid selectively inhibits a specific function of influenza virus, namely the influenza virion-associated RNA polymerase, while it does not affect either of the corresponding host cell polymerases, that is calf thymus DNA dependent RNA polymerase A and B. The said polymerases are enzymes which catalyze the synthesis of RNA in the host cell. It has also been found that phosphonoformic acid inhibits a specific function of herpes virus, namely the induced herpes simplex type 1 DNA polymerase. It is not active on E. coli DNA dependent RNA polymerase and Micrococcus lysodeicticus DNA dependent DNA polymerase. Inhibition of the viral polymerases means that the virus cannot replicate and thus the viral infection is prevented.

The phosphonoformic acid may be formulated for use in human and veterinary medicine for therapeutic and prophylactic use. The compounds may be used in the form of a physiologically acceptable salt. Suitable salts are e.g. amine salts, e.g. dimethylamine and triethylamine salt, ammonium salt, tetrabutylammonium salt, cyclohexylamine salt, dicyclohexylamine salt; and metal salts, e.g. mono-, di- and trisodium salt, mono-, di- and tripotassium salt, magnesium salt, calcium salt and zinc salt.

In clinical practice the phosphonoformic acid will normally be administered topically, orally, intranasally, by injection or by inhalation in the form of a pharmaceutical preparation comprising the active ingredient in the form of the original compound or optionally in the form of a pharmaceutically acceptable salt thereof, in association wjth a pharmaceutically acceptable carrier which may be a solid, semi-solid or liquid diluent or an ingestible capsule, and such preparations comprise a further aspect of the invention. The compound may also be used without carrier material. As examples of pharmaceutical preparations may be mentioned tablets, drops such as nasal drops, preparations for topical application such as ointments, jellies, creams and suspensions, aerosols for inhalation, nasal spray, liposomes, etc. Usually the active substance will comprise between 0.05 and 99, or between 0.1 and 99% by weight of the preparation, for example between 0.5 and 20% for preparations intended for injection and between 0.1 and 50% for preparations intended for oral administration. In addition, the present invention may be practiced by the treatment of virus infections in animals and may by the method in which the phosphonoformic acid or a pharmaceutically acceptable salt thereof is formed in the body.

To produce pharamaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax ® or other polyethylene glycol waxes and compressed to form tablets or cores for dragees. If dragées are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol as a plasticizer, or similar closed capsules, the active substance may be admixed with a Carbowax ® or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as a physiologically inert plastic substance.

In order to obtain dosage units of oral preparations —tablets, capsules etc.—which are designed so as to prevent release of and possible decomposition of the active substance in the gastric juice, the tablets, dragées etc. may be enteric-coated, that is provided with a layer of a gastric juice-resistant enteric film or coating having such properties that it is not dissolved at the acidic pH in the gastric juice. Thus, the active substance will not be released until the preparation reaches the intestines. As example of such known enteric coatings may be mentioned cellulose acetate phtalate, hydroxypropyl-methylcellulose phtalates such as those sold under the trade names HP 55 and HP 50, and Edragit ®L and Eudragit ®S.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbid acid, and citric acid, and for example aroma.

Liquid preparations for oral application may be in the form of elixirs, syrups or suspensions, for example solutions containing from about 0.1% to 20% by weight of active substance, sugar and a mixture or ethanol, water, glycerol, propylene glycol and optionally aroma, saccharine and/or carboxymethylcellulose as a dispersing agent.

For parenteral application by injection preparations may comprise an aqueous solution of a water soluble pharmaceutically acceptable salt of the active acids according to the invention, desirably in a concentration of 0.5-10%, and optionally also a stabilizing agent and/or buffer substances in aqueous solution. Dosage units of the solution may advantageously be enclosed in ampoules.

For topical application, especially for the treatment of herpes virus infections on skin, the preparations are suitably in the form of an ointment, gel, suspension, cream or the like. The amount of active substance may vary, for example between 0.05-20% by weight of the active substance. Such preparations for topical application may be prepared in known manner by mixing the active substance with known carrier materials such as isopropanol, glycerol, paraffin, stearyl alcohol, polyethylene glycol, etc. The pharmaceutically acceptable carrier may also include a known chemical absorption promoter. Examples of absorption promoters are e.g. dimethylacetamide (U.S. Pat. No. 3,472,931), trichloro-ethanol or trifluoroethanol (U.S. Pat. No. 3,891,757), certain alcohols and mixtures thereof (British Pat. No. 1,001,949). A carrier material for topical application to unbroken skin is also described in the British patent specification No. 1,464,975, which discloses a carrier material consisting of a solvent comprising 40-70% (v/v) isopropanol and 0-60% (v/v) glycerol, the balance, if any, being an inert constituent of a diluent not exceeding 40% of the total volume of solvent.

The dosage at which the active ingredients are administered may vary within a wide range and will depend on various factors such as for example the severity of the infection, the age of the patient, etc., and may have to be individually adjusted. As a possible range for the amount of phosphonoformic acid which may be administered per day may be mentioned from about 0.1 mg to about 2000 mg or from about 1 mg to about 2000 mg.

The pharmaceutical compositions containing the active ingredients may suitably be formulated so that they provide doses within these ranges either as single dosage units or as multiple dosage units.

Thus, it has been found according to the invention that phosphonoformic acid, and the physiologically acceptable salts thereof can be used to selectively inhibit viral functions of herpes virus and influenza virus. Since the functions in question are essential for the replication of the virus, phosphonoformic acid and physiologically acceptable salts thereof are useful in therapeutic and/or prophylactic treatment of virus infections.

The preferred aspect of the invention is the use of phosphonoformic acid or a physiologically acceptable salt thereof, in the treatment of herpes virus infections.

Phosphonoformic acid is a known compound. Its synthesis and its trisodium salt are described e.g. by Nylén, Chem. Berichte 57B: 1023–1038 (1924). Since phosphonoformic acid is unstable in its free acid form, it is preferably used in the form of its salts.

BIOLOGICAL TESTS

The Inhibiting effect of phosphonoformic acid on influenza and herpes virus was tested using the methods described below. The test method for testing of the effect of phosphonoformic acid on host cell functions are also described below. In the experiments A–K phosphonoformic acid was used in the form of its trisodium salt.

I. Inhibition of viral and cellular polymerases

Polymerase, nucleic acid template, nucleoside triphosphates, of which guanosine triphosphate is tritium-lbelled, salt and buffer are mixed at 0° C. in a total volume of 125 μl (for herpes DNA polymerase, see F. below). The concentrations of the nucleoside triphosphates UTP (uridine triphosphate), CTP (cytidinetriphosphate), GTP (guanosinetriphosphate) and ATP (adenosinetriphosphate) were generally 400, 400, 400, and 2000 μM, respectively. The test compound is also added in various concentrations to the mixture obtained. A standard mixture without test compound is also prepared using the same amounts of the ingredients. The enzyme reaction, i.e. synthesis of nucleic acid, is started by incubating the mixture at 37° C. For influenza RNA polymerases the temperature is 33° C. The reaction is allowed to proceed for 60 minutes in the assay of influenza and Micrococcus polymerases. For E. coli DNA dependent RNA polymerase the time is 20 min. and for herpes DNA polymerase 30 minutes. The incubation time for calf thymus polymerases is 10 minutes. The incorporation of labelled monomer into trichloroacetic acid insoluble nucleic acid product was measured in the following way. Before and after the incubation period 50 μl are withdrawn from the mixture and applied to filter discs. These are put in 5% trichloroacetic acid solution and washed several times. After drying the discs are measured for radioactivity in a liquid scintillation counter. the difference in radioactivity between samples with and without added compound is used to calculate the inhibition of the polymerase activity. The inhibition is expressed as percentage inhibition using the radioactivity of the standard sample as basis.

A. Inhibition by phosphonoformic acid of type A influenza virion associated RNA polymerase Influenza $A_2$ Aichi virus was purified according to the method of Pons and Hirst, Virology 34 385 (1968). The assay mixture is described by Bishop, Obijeski and Simpson, J. Virol. 8 66 (1971). The inhibitory effect of phosphonoformic acid is shown in Table 1 below.

Table 1

| Inhibition by phosphonoformic acid of type A influenza virion-associated RNA polymerase | |
|---|---|
| Conc. of phosphonoformic acid (μM) | Inhibition[a] (%) |
| 0.1 | 21 |
| 0.50 | 67 |
| 1.00 | 79 |
| 10 | 91 |
| 100 | 95 |
| 500 | 93 |

[a]mean of two experiments

B. Inhibition by phosphonoformic acid of type B influenza virionassociated RNA polymerase Polymerase from influenza B Hongkong 8/73 was assayed in the same way as for influenza $A_2$ Aichi in experiment A. The inhibitory effect of phosphonoformic acid is shown in Table 2 below.

Table 2

| Inhibition by phosphonoformic acid of Type B influenza virion associated RNA polymerase[a] | |
|---|---|
| Conc. of phosphonoformic acid (μM) | Inhibition (%) |
| 1.0 | 77 |
| 500 | 100 |

[a]In this experiment the concentration of GTP was 135 μM.

C. Inhibition by phosphonoformic acid of calf thymus DNA dependent RNA polymerase Purification of the enzymes was carried out according to the method of Kedinger et al, Eur. J. Biochem. 28 269 (1972). The enzyme fractions DCB and DCA were used for all experiments. The assay mixture of Kedinger, loc.cit., was used. The test results are given in Table 3 below.

Table 3

| Inhibition by phosphonoformic acid of calf thymus DNA dependent RNA polymerase fractions B and A | | |
|---|---|---|
| Conc. of phosphonoformic acid (μM) | Inhibition % | |
|  | DCB | DCA |
| 500 | 0 | −3 |

D. Inhibition by phosphonoformic acid of E. coli DNA dependent RNA polymerase

The enzyme was bought from Sigma. The template used was DNA extracted from E. coli according to Marmur, J. Mol. Biol. 3 208 (1961) and the assay mixture essentially that described by Burgess, J. Biol. Chem. 244 6160 (1969). The test results are given in Table 4.

Table 4

| Inhibition by phosphonoformic acid of E. coli dependent RNA polymerase | |
|---|---|
| Conc. of phosphonoformic acid (μM) | Inhibition (%) |
| 500 | 3 |

E. Inhibition by phosphonoformic acid of Micrococcus luteus DNA dependent DNA polymerase The polymerase was bought from Sigma and assayed essentially according to Harwood et al., J. Biol, Chem. 245 5614 (1970).

The test results are given in Table 5 below.

Table 5

| Inhibition by phosphonoformic acid of Micrococcus luteus DNA dependent DNA polymerase | |
|---|---|
| Conc. of phosphonoformic acid (μM) | Inhibition (%) |
| 500 | 6 |

F. Inhibition by phosphonoformic acid of herpes simplex virus type 1 induced DNA polymerase Purification of the enzyme was carried out according to the method of Weissbach et al., J. Biol. Chem. 248 6270 (1973).

The assay mixture (200 μl) contained 200 μg/ml activated calf thymus DNA and 0.05 mM [3H] dTTP (specific activity 130 cpm per pmole).

All other ingredients were according to Weissbach (see above).

The results are given in table 6.

Table 6

| Inhibition by phosphonoformic acid of herpes simplex virus type 1 induced DNA polymerase | |
|---|---|
| Conc. of phosphonoformic acid (μM) | Inhibition (%) |
| 5 | 15 |
| 20 | 43 |
| 100 | 76 |
| 500 | 90 |

II. Inhibition of virus multiplication in cell cultures

The inhibition of influenza virus and herpes virus by phosphonoformic acid has been measured as plaque reduction according to the following procedures.

G. Inhibition by phosphonoformic acid of influenza (WSN Wilson Smith Neurotropic type A.) plaque The method for plaque assay of influenza has been described by Bentley et al., Archiv fur die Gesamte Virusforschung 33 (1971) 234. Monolayers of MDCK (Mardin Darby Canine Kidney) cells on 5 cm plastic petri dishes were inoculated with 100 plaque-forming units of influenza virus (WSN). After virus adsorption, 5 ml of agarose overlay containing different concentrations of phosphonoformic acid was added and the plates were incubated at 34° C. for 4 days. The plaques formed at this time were counted. The results are shown in Table 7.

Table 7

| Inhibition by phosphonoformic acid of influenza virus (WSN) plaque on MDCK monolayers. | |
|---|---|
| Conc. of phosphonoformic acid (μM) | Inhibition[a] (%) |
| 100 | 10 |
| 250 | 50 |
| 500 | 95 |

[a] a mean of three different experiments

H. Inhibition by phosphonoformic acid of herpes simplex type 1 plaque

The plaque reduction assay for herpes simplex type 1 was performed on GMK (Green Monkey Kidney) cells as described by Ejereito et el., J. Gen. Virol. 2 (1968) 357. Monolayers on 5 cm petri dishes were used and after virus adsorption phosphonoformic acid was added in the medium. The results are shown in table 8.

Table 8

| Inhibition by phosphonoformic acid of herpes simplex type 1 plaque on GMK monolayers. | |
|---|---|
| Conc. of phosphonoformic acid (μM) | Inhibition[a] (%) |
| 1 | 0 |
| 15 | 50 |
| 100 | 90 |

[a] means of three different experiments

I. Inhibition by phosphonoformic acid of herpes simplex type 2 plaque

The plaque reduction assay for herpes simplex type 2 was performed in the same way as in experiment H. The results are shown in table 9.

Table 9

| Inhibition by phosphonoformic acid of herpes simplex type 2 patient isolates plaque on SIRC (Staatens Seruminstitut Rabbit Cornea) monolayers. | |
|---|---|
| Conc. of phosphonoformic acid (μM) | Inhibition (%) |
| 500 | >99.9 |

J. Acute toxicity

Phosphonoformic acid was tested for acute toxicity in mice. The compound (as its sodium salt) was given as solution i.p. in doses of 250, 500, 1000, 2000, and 4000 μmol/kg. Groups of 4 male mice of NMRI strain weighing 18.5–20.5 g were used for each dose. LD50 was found to be between 4000 and 2000 μmole/kg bodyweight.

K. Other animal experiments

Preliminary experiments on cutaneous herpes type 1 infected guinea pigs have shown that phosphonoformic acid as its trisodium salt in topical preparations according to examples 15, 16 and 17 below has a therapeutic effect.

Discussion of the test results

The purpose of tests A. B and G above is to ascertain the effect of the phosphonoformic acid against influenza viruses. The purpose of tests F, H and I is to ascertain the effect of phosphonoformic acid against herpes viruses. The purpose of test C, D and E is to ascertain the absence of effect of phosphonoformic acid on cellular polymerases. As seen in tables 1 and 2, respectively, phosphonoformic acid inhibits the influenza A virus polymerase activity to more than 50% at a concentration of 0.5 μM and influenza B virus polymerase to more than 50% at a concentration of 1.0 μM. As seen in table 7, phosphonoformic acid inhibits the corresponding plaque formation to 50% at a concentration of 250 μM. As seen in tables 6, 8 and 9, respectively, phosphonoformic acid inhibits the herpes simplex virus type 1 induced DNA polymerase activity to more than 50% at a concentration of 100 μM, the plaque formation of herpes simplex virus type 1 to 50% at a concentration of 15 μM and plaque formation of the herpes virus type 2 to more than 99.9% at 500 μM. In tables 3, 4 and 5 it is seen that phosphonoformic acid has no significant effect against calf thymus DNA dependent RNA polymerases, or 0% and −3% inhibition respectively, at a concentration of 500 μM; that it is practically inactive against E. coli DNA dependent RNA polymerase, or 3% inhibition at a concentration of 500 μM, and that it is practically inactive against Micrococcus luteus DNA dependent DNA polymerase, or 6% inhibition at a concentration of 500 μM. The acute toxicity of phosphonoformic acid is low, i.e. LD50 between 2000 and 4000 μmole/kg i.p. in mice. Thus, phosphonoformic acid exerts a selective effect on influenza and herpes viruses. The selective effect of phosphonoformic acid on the viral polymerases gives a molecular basis for a selective antiviral effect in animals including man.

Salts of phosphonoformic acid

Physiologically acceptable salts of phosphonoformic acid are prepared by methods known in the art as illustrated in the following. Metal salts can be prepared by reacting a metal hydroxide with an alkylester of phosphonoformic acid. Examples of metal salts of phosphonoformic acid which can be prepared in this way are salts containing Li, Na, K, Ca, Mg, Zn, Mn and Ba. A less soluble metal salt can be precipitated from a solution of a more soluble salt by addition of a suitable metal compound. Thus for examples, Zn, Mg and Mn salts of phosphonoformic acid can be prepared from phosphonoformic sodium salts. The metal ion of a metal salt of phosphonoformic acid can be exchanged by hydrogen ions, other metal ions, ammonium ion and ammonium ions substituted by one or more organic radicals by using a cation exchanger as shown in the following examples.

EXAMPLE 1. Disodium salt of phosphonoformic acid

Phosphonoformic acid trisodium salt (1.30 g) was dissolved in 50 ml of water. To this solution a cation exchanger Dowex 50 W×2 in acid form was added with stirring until a pH of 5.35 was obtained. The ion exchanger was filtered off and the filtrate evaporated at a reduced pressure. The residue was triturated with ethanol with cooling. The yield of disodium salt was 0.65 g. It contained 8.3% water. Titration as base gave equivalent weight 168.2 (corrected for 8.3% water) and Na 27.3% (corrected for water). Calculated for $CHO_5P\cdot 2Na$, formula weight 170.0, Na 27.1%.

EXAMPLE 2. Monocyclohexylammonium salt of phosphonoformic acid

A cation exchanger Dowex 50 W×2 (75 g) on acid form was saturated with cyclohexylamine (10 g), poured into a column (diameter 2 cm) and washed free from excess of cyclohexylamine. A water solution of phosphonoformic acid trisodium salt (1.3 g in 40 ml of water) was slowly passed through the column followed by about 100 ml of water and the combined eluate evaporated at a reduced pressure. The salt obtained was recrystallized from ethanol-water. The final product was crystalline and hand a melting-point of 215°–218° C. (decomposition) and contained 27.0% of water. Titration as acid gave equivalent weight 220.5 (corrected for 27.0% water). Calculated for $CH_3O_5P\cdot C_6H_{13}N$ formula weight 225.2. The NMR spectrum indicated that the salt contained only one cyclohexylamine residue (a minor impurity in form of ethanol was detected).

Examples of other useful salts which can be prepared in this way are the salts of the formula

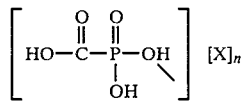

in which formula n is 1, 2 or 3 and X is a salt-forming component such as $NH_3$, $CH_3NH_2$, $C_2H_5NH_2$ $C_3H_7NH_2$, $C_4H_9NH_2$, $C_5H_{11}NH_2$, $C_6H_{13}NH_2$, $(CH_3)_2NH$, $(C_2H_5)_2NH$, $(C_3H_7)_2NH$, $(C_4H_9)_2NH$, $(C_5H_{11})_2NH$, $(C_6H_{13})_2NH$, $(CH_3)_3N$, $(C_2H_5)_3N$, $(C_3H_7)_3N$, $(C_4H_9)_3N$, $(C_5H_{11})_3N$, $(C_6H_{13})_3N$, $C_6H_5CH_2NH_2$, $HOCH_2CH_2NH_2$, $(HOCH_2CH_2)_2NH$, $(HOCH_2CH_2)_3N$, $C_2H_5NH(CH_2CH_2OH)$, $C_2H_5N(CH_2CH_2OH)_2$, $(HOH_2C)_3CNH_2$ and

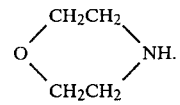

Further examples of other useful salts which can be prepared by the ion exchange technique are quaternary ammonium salts of phosphonoformic acid, i.e. salts in which 1–3 of the hydrogens in phosphonoformic acid (structural formula I) have nbeen substituted with quaternary ammonium ions such as $(CH_3)_4N$, $(C_2H_5)_4N$, $(C_3H_7)_4N$, $(C_4H_9)_4N$, $(C_5H_{11})_4N$, $(C_6H_{13})_4N$ and $C_2H_5N(CH_2CH_2OH)_3$. Lipophilic salts of this type can also be prepared by mixing a salt of phosphonoformic acid with a quaternary ammonium salt in water and extracting out the resulting quaternary ammonium salt of phosphonoformic acid with an organic solvent such as dichloromethane, chloroform, ethyl acetate and methyl isobutyl ketone.

Pharmaceutical compositions

The following examples illustrate the preparation of pharmaceutical compositions of the invention. The phosphonoformic acid is preferably used in the form of its sodium salt.

EXAMPLE 3. Aerosol for inhalation

| | |
|---|---|
| Phosphonoformic acid (as its trisodium salt) | 1.00 g |
| Miglyol ® | 0.20 g |
| Frigen ® 11/12/113/114 | ad 100.0 g |

EXAMPLE 4. Tablets

| | |
|---|---|
| Each tablet contains: | |
| Phosphonoformic acid (as its trisodium salt) | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

EXAMPLE 5. Suppositories

| | |
|---|---|
| Each suppository contains: | |
| Phosphonoformic acid (as its trisodium salt) | 20.0 mg |
| Ascorbyl palmitate | 1.0 mg |
| Suppository base (Imhausen H or Witepsol ® H) | ad 2000.0 mg |

EXAMPLE 6. Syrup

| | |
|---|---|
| Phosphonoformic acid (as its trisodium salt) | 0.200 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water | ad 100.0 g |

EXAMPLE 7. Injection solution

| | |
|---|---|
| Phosphonoformic acid (as its trisodium salt) | 0.500 mg |
| Sodium pyrosulfite | 0.500 mg |
| Disodium edetate | 0.100 mg |
| Sodium chloride | 8.500 mg |
| Sterile water for injection | ad 1.00 ml |

EXAMPLE 8. Inhalation solution

| | |
|---|---|
| Phosphonoformic acid (as its trisodium salt) | 5.00 g |
| Sodium pyrosulfite | 0.10 g |
| Disodium edetate | 0.10 g |
| Sodium chloride | 0.85 g |
| Purified water | ad 100.0 ml |

EXAMPLE 9. Sublingual tablets

| | |
|---|---|
| Phosphonoformic acid (as its trisodium salt) | 5.0 mg |
| Lactose | 85.0 mg |
| Talc | 5.0 mg |
| Agar | 5.0 mg |
| | 100.0 mg |

EXAMPLE 10. Drops

| | |
|---|---|
| Phosphonoformic acid (as its trisodium salt) | 2.00 g |
| Ascorbic acid | 1.00 g |
| Sodium pyrosulfite | 0.10 g |
| Disodium edetate | 0.10 g |
| Liquid glucose | 50.00 g |
| Absolute alcohol | 10.00 g |
| Purified water | ad 100.0 ml |

EXAMPLE 11. Syrup

| | |
|---|---|
| Phosphonoformic acid (as its trisodium salt) | 0.200 g |
| Liquid glucose | 30.0 g |
| Sucrose | 50.0 g |
| Ascorbic acid | 0.1 g |
| Disodium edetate | 0.01 g |
| Orange essence with solubilizer | 0.25 g |
| Hydrochloric acid to pH 6.0–6.5 | |
| Purified water | ad 100.0 g |

EXAMPLE 12. Solution for injection

| | |
|---|---|
| Phosphonoformic acid (as its trisodium salt) | 0.500 mg |
| Disodium edetate | 0.100 mg |
| Sodium chloride | 8.500 mg |
| Hydrochloric acid to pH 6.5–7.0 | |
| Sterile water for injection | ad 1.00 ml |

EXAMPLE 13. Solution for inhalation

| | |
|---|---|
| Phosphonoformic acid (as its trisodium salt) | 5.00 g |
| Disodium edetate | 0.10 g |
| Sodium chloride | 0.85 g |
| Hydrochloric acid to pH 6.5–6.9 | |
| Purified water | ad 100.0 ml |

EXAMPLE 14. Drops

| | |
|---|---|
| Phosphonoformic acid (as its trisodium salt) | 2.00 g |
| Citric acid | 1.00 g |
| Disodium edetate | 0.10 g |
| Liquid glucose | 50.00 g |
| Ethanol 95% | 10.00 g |
| Sodium hydroxide and hydrochloric acid to pH 6.2–6.8 | |
| Purified water | ad 100.0 ml |

EXAMPLE 15. Solution for topical use

| | |
|---|---|
| Phosphonoformic acid (as its trisodium salt) | 2.00 g |
| Isopropanol | 38.0 g |
| Glycerol | 13.6 g |
| Hydrochloric acid to pH 5.0–7.0 | |
| Purified water | ad 100.0 g |

Preparations containing 0.2, 0.5 and 1.0 g of phosphonoformic acid trisodium salt have also been prepared.

EXAMPLE 16. Jelly

| | |
|---|---|
| Phosphonoformic acid (as its trisodium salt) | 4.0 g |
| Methocel ® | 4.0 g |
| Methyl paraoxybenzoate | 0.12 g |
| Propyl paraoxybenzoate | 0.05 g |
| Sodium hydroxide and hydrochloric acid to pH 6.7 | |
| Destilled water | ad 100.0 ml |

EXAMPLE 17. Ointment I

| | |
|---|---|
| Phosphonoformic acid (as its trisodium salt) | 2.5 g |
| Cetyltrimethylammonium bromide | 0.6 g |
| Stearyl alcohol | 2.25 g |
| Cetanol | 6.75 g |
| Liquid paraffin | 17.0 g |
| Glycerol | 12.0 g |
| Hydrochloric acid to pH 6.5 | |
| Destilled water | ad 100.0 g |

Preparations containing 0.2, 0.5, 1.0 and 2.0 g of phosphonoformic acid trisodium salt have also been prepared.

EXAMPLE 18. Ointment II

| | |
|---|---|
| Phosphonoformic acid (as its trisodium salt) | 2.5 g |
| Polyethylene grycol 1500 | 50 g |
| Polyethylene glycol 4000 | 15 g |
| Propylene glycol | ad 100 g |

EXAMPLE 19. Ointment III

| | |
|---|---|
| Phosphonoformic acid (as its trisodium salt) | 3.0 g |
| Sorbitan monoleate | 5.0 g |
| Petrolatum | ad 100 g |

EXAMPLE 20. Gastric juice-resistant tablets

Tablets according to Example 4 are coated with an enteric coating solution with the following composition:

| | |
|---|---|
| Cellulose acetate phtalate | 120.0 g |
| Propylene glycol | 30.0 g |
| Sorbitan monoleate | 10.0 g |
| Ethanol 95% | 450.0 ml |
| Acetone | q.s. ad 1000.0 ml |

The coating is carried out by a pouring procedure in a conventional coating pan or by spraying the tablets in a pan spray tablet coater.

What we claim is:

1. A method for the selective treatment of virus infections in an animal or human host comprising administering to said host so infected an amount effective to treat said virus infection of phosphonoformic acid or a physiologically acceptable salt thereof.

2. A method according to claim 1 for the treatment of infections caused by herpes viruses.

3. A method according to claim 1 for the treatment of infections caused by herpes simplex type 1 viruses.

4. A method according to claim 1 for the treatment of infections caused by herpes simplex type 2 viruses.

5. A method according to claim 1 for the treatment of infections caused by varicella (Herpes zoster) viruses.

6. A method according to claim 1 for the treatment of infections caused by cytomegalo viruses.

7. A method according to claim 1 for the treatment of infections caused by Epstein-Barr viruses.

8. A method according to claim 1 for the treatment of infections caused by influenza viruses.

9. A method according to claim 1 for the treatment of infections caused by influenza type A or B viruses.

10. A method according to claim 1 for the treatment of infections caused by influenza type A viruses.

11. A method according to claim 1 for the treatment of infections, caused by papilloma viruses.

12. A method according to claim 1 for the treatment of herpes dermatitis, herpes genitalis, herpes keratitis and herpes encephalitis.

13. A method according to claim 1 for the treatment of herpes zoster.

14. A method according to claim 1 for the treatment of infectious mononucleosis.

15. A method according to claim 1 for the treatment of influenza.

16. A method according to claim 1 for the treatment of warts.

17. A method according claim 1, comprising topical administration of phosphonoformic acid or a physiologically acceptable salt thereof.

* * * * *

UNITED STATES PATENT AND TRADEMARK OFFICE

CERTIFICATE EXTENDING PATENT TERM
UNDER 35 U.S.C. § 156

PATENT NO.:      4,215,113

DATED:           July 29, 1980

INVENTORS:       Bertil F. H. Eriksson et al.

PATENT OWNER:    Aktiebolaget Astra

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

1,042 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks